US008675201B2

(12) United States Patent
Liu et al.

(10) Patent No.: US 8,675,201 B2
(45) Date of Patent: Mar. 18, 2014

(54) COHERENT ANTI-STOKES RAMAN HOLOGRAPHY (75) Inventors: Zhiwen Liu, State College, PA (US); Kebin Shi, State College, PA (US); Demetri Psaltis, St-Sulpice (CH); Qian Xu, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 880 days.

(21) Appl. No.: 12/793,976

(22) Filed: Jun. 4, 2010

(65) Prior Publication Data
US 2010/0309465 A1 Dec. 9, 2010

Related U.S. Application Data (60) Provisional application No. 61/184,529, filed on Jun. 5, 2009.

(51) Int. Cl.
*G01B 9/021* (2006.01)

(52) U.S. Cl.
USPC .......................................................... 356/457

(58) Field of Classification Search
USPC ........................................ 356/301, 457, 458
See application file for complete search history.

(56) References Cited

U.S. PATENT DOCUMENTS

| 4,405,237 A | 9/1983 | Manuccia et al. |
| 4,512,660 A | 4/1985 | Goldberg |
| 5,303,710 A | 4/1994 | Bashkansky et al. |
| 6,108,081 A | 8/2000 | Holtom et al. |
| 6,798,507 B2 | 9/2004 | Xie et al. |
| 6,809,814 B2 | 10/2004 | Xie et al. |
| 7,092,086 B2 | 8/2006 | Knebel |
| 7,289,203 B2 | 10/2007 | Frankel |
| 7,403,688 B2 | 7/2008 | Knox et al. |
| 7,471,430 B1 | 12/2008 | Andersen |
| 2002/0191239 A1 | 12/2002 | Psaltis et al. |
| 2007/0247620 A1* | 10/2007 | Koo .............................. 356/301 |
| 2009/0067018 A1 | 3/2009 | Pu et al. |
| 2010/0091292 A1* | 4/2010 | Pfaff ............................. 356/457 |

OTHER PUBLICATIONS

Shi et al., "Coherent anti-Stokes Raman holography for chemically selective single-shot nonscanning 3D imaging", *Physical Review Letters*; 104(9), Mar. 5, 2010.
Brady et al., "Compressive Holography", *Optics Express*, 17(15):13040-13049, 2009.
Cheng, Ji-Xin et al., "Coherent Anti-Stokes Raman Scattering Microscopy: Instrumentation, Theory, and Applications", J. Phys. Chem. B., 108(3), 827-829, 2004.

* cited by examiner

*Primary Examiner* — Hwa Lee
(74) *Attorney, Agent, or Firm* — Gifford, Krass, Sprinkle, Anderson & Citkowski, P.C.

(57) ABSTRACT

Apparatus and methods of four wave mixing (FWM) holography are described, including illuminating a sample with a first beam, a second beam, and a third beam, and combining the generated FWM signal with a reference beam at a imaging device to obtain holographic image data. In some examples, the first and second beams may be provided by a single pump-probe beam. The third beam may be a Stokes beam or an anti-Stokes beam. A representative example is coherent anti-Stokes Raman holography (CARS holography), which includes illuminating a sample with a pump/probe beam and a Stokes beam to obtain a CARS signal from the sample; and combining the CARS signal with a reference beam to obtain a CARS hologram.

24 Claims, 8 Drawing Sheets

COHERENT ANTI-STOKES RAMAN HOLOGRAPHY

REFERENCE TO RELATED APPLICATIONS

This patent application claims priority from U.S. provisional patent application Ser. No. 61/184,529, filed Jun. 5, 2009, the entire content of which is incorporated herein by reference.

REFERENCE TO GOVERNMENT SPONSORSHIP

This invention was made with government support under contract numbers DBI-0649866 and ECCS-0547475 awarded by the National Science Foundation. The government has certain rights in the invention.

FIELD OF THE INVENTION

The present invention relates to spectroscopy, holography, and imaging, in particular to holographic imaging.

BACKGROUND OF THE INVENTION

CARS (coherent anti-Stokes Raman scattering) is a type of nonlinear vibrational spectroscopy. CARS microscopy has been used previously, however scanning is hitherto required in order to perform three-dimensional (3D) imaging. This makes imaging complex, and makes it difficult to apply existing CARS microscopy techniques to imaging fast physical or chemical processes in 3D.

However, CARS has great chemical selectivity, so improved imaging methods using this technique would be extremely valuable for numerous applications. Similarly, other FWM (four wave mixing) imaging methods would be very useful.

SUMMARY OF THE INVENTION

An example four-wave mixing (FWM) holography apparatus for characterizing a sample comprises a sample illumination system configured to illuminate the sample with a first beam (pump beam), a second beam (probe beam), and a third beam (e.g. a Stokes beam), so as to generate a four-wave mixing (FWM) signal (the fourth beam). The first and second beams can be physically the same beam, referred to as a pump/probe beam. A reference beam then combines with the FWM signal to form a FWM hologram at an imaging device, which may be an electronic imaging device (such as an electronic image sensor), analog recording medium, or any other holographic recording device. The reference beam has a frequency which is matched to the FWM signal. A FWM hologram may be an in-line or off-axis hologram.

Examples of the present invention include methods and apparatus for four wave mixing (FWM) holography, such as coherent anti-Stokes Raman (CARS) holography. CARS holography allows non-scanning 3D CARS imaging, which can capture both the amplitude and the phase of a wide-field CARS image. CARS microscopy uses molecular vibrational response as the contrast mechanism. CARS has significantly improved sensitivity over spontaneous Raman scattering. Examples relating to CARS holography can be adapted to obtain other FWM holographic methods. CARS is an example of FWM, and examples of the present invention include CARS and other examples of FWM holography.

In an example approach, a sample is illuminated by a pump/probe beam (having a pump/probe frequency, $\omega_p$) and a Stokes beam (having a Stokes frequency $\omega_s$). CARS generated from the sample (having CARS frequency $2\omega_p - \omega_s$) is combined with a reference beam to produce a CARS hologram. The holographic information can be recovered from data collected from the imaging device, such as an electronic imaging device.

A Stokes beam and a reference beam at the CARS frequency can be generated together using an optical parametric oscillator (OPO). Tuning the OPO allows the Stokes beam and the reference beam to be tuned together using the OPO while retaining the proper relationship between the frequencies.

An example apparatus includes a source generating the pump/probe beam, a frequency doubler generating a doubled frequency beam, and an optical parametric oscillator receiving the doubled frequency beam and generating the Stokes beam and the reference beam. The Stokes beam and the pump/probe beam are both incident on the sample, and the CARS radiation is collected and combined with the reference beam to form a hologram at the imaging device, for example at the imaging surface of an electronic image sensor.

The radiation source may comprise a pulsed laser, or other pulsed radiation source, a continuous wave laser, or other radiation source. One or more beam splitters may be used to divide the source radiation, for example into a pump/probe beam and an input beam to frequency doubler or other nonlinear element(s). All beams may be obtained from a single pulsed laser using nonlinear elements to obtain the desired frequencies.

Coherent anti-Stokes Raman holography (CARS holography) captures both the amplitude and the phase of a coherent Raman image. Hence, CARS holography allows non-scanning, chemically selective, three-dimensional imaging at a laser pulse duration limited speed. In some examples, a CARS hologram (or other FWM hologram) can be captured in a single shot (i.e. a single laser pulse per beam), which is not possible to achieve by using any existing laser scanning based Raman imaging techniques.

Experimental results showed that a CARS hologram can be recorded in a single shot, allowing three-dimensional (3D) imaging of fast dynamic phenomena at laser pulse-width limited speed (e.g., nanosecond or pico-second time scale).

The presence of an intense reference beam (i.e., local oscillator) and the coherent homodyne detection nature of CARS holography can also potentially lead to shot noise limited detection sensitivity.

A method of four-wave mixing holography (FWM holography) imaging of a sample comprises obtaining a FWM signal from the sample, and combining the FWM signal with a reference beam to obtain a FWM hologram. The FWM signal is generated by nonlinear wave mixing of multiple beams (e.g. a pump/probe and a Stokes beam) at the sample, and the reference with matched frequency to the FWM signal may be generated using a nonlinear medium.

A pump/probe beam may comprise one or more pulses of laser radiation from a pulsed laser, and the Stokes beam and the reference beam can be generated by a nonlinear optical device receiving frequency doubled pulsed laser radiation. The nonlinear optical device may be an optical parametric oscillator (OPO).

A FWM hologram may be a coherent anti-Stokes Raman hologram (CARS hologram), a coherent Stokes Raman hologram (CSRS hologram), a stimulated Raman hologram, a Brillouin scattering hologram, or a FWM hologram originating from electronic responses.

In some inline holography examples, the FWM signal and the reference beam propagate co-linearly. The reference beam may be generated by a nonlinear material located proximate or adjacent the sample. The sample may be stacked with a layer of nonlinear material used to generate the reference beam. In some examples, the FWM signal and the reference beam converge or otherwise combine to form the hologram on an electronic image sensor, an image being formed by processing of electronic sensor data.

Examples of the present invention also include multiplex FWM holography, in which a plurality of holograms is captured. In representative examples, the reference beam and at least one of the three beams (e.g. the third beam, such as the Stoke or anti-Stokes beam) are broadband beams, so as to generate a plurality of FWM holograms having different spatial carrier frequencies. The hologram carrier frequency can be selected to form an image of a selected FWM process (e.g., corresponding to a selected vibrational transition) within the sample.

A method of obtaining a FWM image (such as a CARS image) of a sample comprises illuminating the sample with multiple beams such as a pump beam, a Stokes beam, and a probe beam, so as to generate a FWM signal, combining the FWM signal with a reference beam to obtain the FWM image, the FWM image being a holographic image including three-dimensional information relating to the sample. The Stokes beam and the reference beam may be generated by the same non-linear element, such as an optical parametric oscillator (OPO). The pump-probe beam may be obtained from pulsed laser radiation, frequency doubled pulsed laser radiation being input to the OPO. A Stokes and/or a reference beam may be wavelength adjusted by tuning the OPO. The image may be a three-dimensional image. The reference beam and the FWM signal may be generally co-linear as they arrive at the electronic image sensor, to form an in-line hologram, or in some examples an off-axis hologram is formed. One or more beams (such as the reference beam and/or a Stokes beam) may be formed using an optical parametric oscillator. The FWM signal and the reference beam interact to form the hologram at the imaging device, which may be an electronic imaging device or an analog recording, such as a film. The image can be formed by processing of the hologram data, such as digital signal processing of electronic imaging device data. In some examples, a FWM image can obtained using a single pulse of illuminating radiation. Using multiplex holography, a plurality of images corresponding to different FWM processes within the sample can be formed by processing multiplex hologram data captured using a single illumination pulse.

A temporal sequence of FWM holograms can be collected to track a dynamic process. For example, a CARS image can be obtained using a single pulse of illuminating radiation, and a temporal sequence of CARS images allows tracking of a dynamic process. An imaged sample need not including a chemical labeling compound.

An example FWM holography apparatus, such as a coherent anti-Stokes Raman (CARS) holography apparatus, comprises a sample illumination system configured to direct a pump-probe beam and a Stokes beam onto the sample, a reference beam source, generating a reference beam; and an imaging device, the imaging device receiving CARS from the sample induced by the pump-probe beam and the Stokes beam and the reference beam, the reference beam and the CARS combining at the imaging device to form the CARS hologram. The pump-probe beam may be obtained from a pulsed laser. An optical parametric oscillator receives frequency doubled radiation from the pulsed laser and generates the Stokes beam and/or the reference beam.

In some examples, a pulsed laser radiation source provides a pump-probe beam incident on the sample, a frequency doubler receives radiation from the pulsed radiation source and generates frequency doubled radiation, and an optical parametric oscillator receives the frequency doubled radiation and generates a Stokes beam (and optionally the reference beam), the Stokes beam being incident on the sample. A sample holder is configured to receive the sample, and may optionally include a non-linear material for generating the reference beam. An imaging device receives the signal (such as CARS) from the sample induced by the pump-probe beam and the Stokes beam, and further receives the reference beam, the reference beam and the CARS signal combining at the imaging device to form a CARS hologram.

An apparatus may include one or more radiation sources, optically linear and/or nonlinear elements, lenses, beamsplitters, beam steering elements, imaging devices and the like or photosensitive optical media (e.g., holographic photopolymer), and the configuration used may be chosen according to the desired application using routine skill in view of the invention described herein.

BRIEF DESCRIPTION OF THE DRAWINGS

FIGS. 2A-2D show chemical selective CARS holographic imaging, where

FIGS. 5A-5F show chemical selective in-line holographic CARS imaging, where

DETAILED DESCRIPTION OF THE INVENTION

Examples of the present invention include non-scanning chemically selective 3D imaging using FWM holography, such as coherent anti-Stokes Raman holography (CARS holography). It is demonstrated that single-shot (~5 ns), nonscanning, 3D CARS holographic imaging of microspheres can be achieved with a speed limited only by the laser pulse duration. Examples below describe CARS holography in detail as representative examples, but the invention is not only related to CARS. For example, other examples of the invention include other FWM holographic methods.

Coherent anti-Stokes Raman scattering (CARS) directly uses molecular vibrational response as a contrast mechanism, and is therefore label-free. Further, CARS can have significantly improved sensitivity over spontaneous Raman scattering.

In an example approach, a pump/probe beam and a tunable Stokes beam with respective angular frequencies $\omega_p$ and $\omega_s$ interact with a sample to produce four wave mixing (FWM) signal, which may be a resonant CARS signal if the frequency difference between the pump and the Stokes ($\omega_p-\omega_s$) matches the molecular vibrational frequency of the sample. A reference beam with angular frequency $2\omega_p-\omega_s$ then interferes with the generated CARS/FWM image to record a digital CARS/FWM hologram. Denoting the reference beam as $Re^{-j(2\omega_p-\omega_s)t}$ and the FWM image as $Se^{-j(2\omega_p-\omega_s)t}$, the hologram is $|R+S|^2$. The complex CARS field S can then be reconstructed from the holographic data.

Single-shot three-dimensional holographic Raman imaging of multiple microspheres was experimentally demonstrated. The laser pulse duration used in the experiment was ~5 ns. The results showed that coherent anti-Stokes Raman (CARS) holography allows non-scanning label-free imaging in three dimensions.

CARS holography captures both the amplitude and the phase of a wide-field CARS image. In essence, it includes the capabilities of both CARS and holography, and allows new approaches for non-scanning chemically selective 3D imaging.

In an example approach, a pump/probe beam and a tunable Stokes beam with respective angular frequencies $\omega_p$ and $\omega_s$ interact with a sample to produce four wave mixing (FWM) signal, or resonant CARS signal if the frequency difference between the pump and the Stokes ($\omega_p-\omega_s$) matches the molecular vibrational frequency of the sample. A reference beam $Re^{-j(2\omega_p-\omega_s)t}$ with angular frequency $2\omega_p-\omega_s$ then interferes with the generated CARS/FWM image $Se^{-j(2\omega_p-\omega_s)t}$ to record a digital or analogue CARS/FWM hologram $|R+S|^2$.

The complex CARS field S can then be reconstructed by the following procedure: first the two-dimensional (2D) Fourier transform of the recorded digital hologram is calculated; then one side band (e.g., corresponding to the terms R*S) is selected through digital filtering; finally, the complex CARS image field can be obtained through the inverse 2D Fourier transform of the selected band. Three-dimensional CARS imaging can then be achieved by digitally propagating the reconstructed complex CARS field. The digital propagation is realized by first taking the 2D Fourier transform of the complex field, then multiplying it by the transfer function $e^{jk_zL}$ (where $k_z=\sqrt{(2\pi/\lambda)^2-k_x^2-k_y^2}$, $\lambda$ is the wavelength in the medium, ($k_x$, $k_y$, $k_z$) is the wave vector, and $|L|$ is the propagation distance), and finally taking the inverse Fourier transform.

Figure 1A:
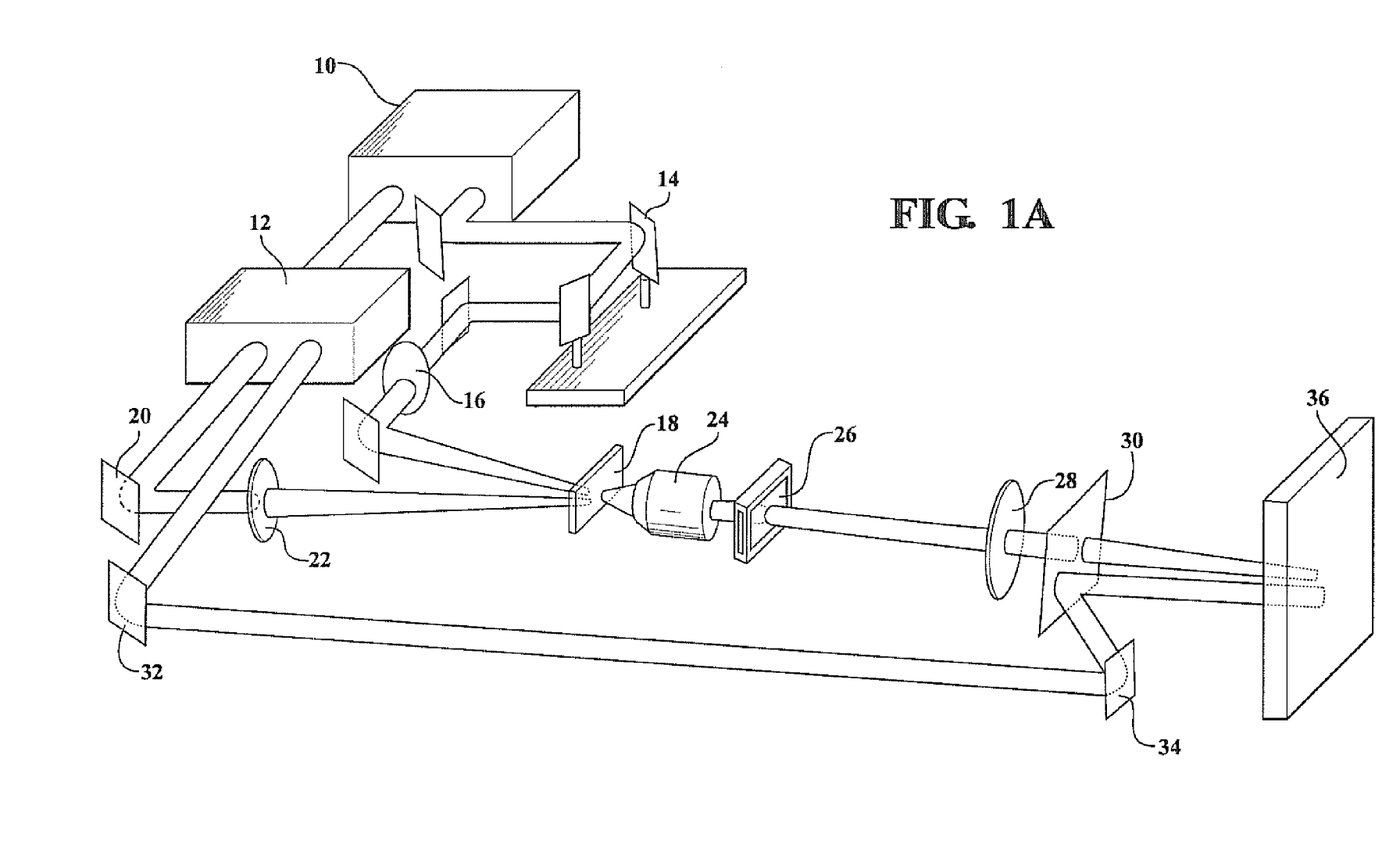
FIG. 1A is a schematic diagram of a FWM holography apparatus.

FIG. 1A is a schematic diagram of an example experimental system. The output from a nanosecond pulsed laser 10 at fundamental angular frequency $\omega_p$ (Continuum Surelite III, $\lambda_1$=1064 nm, repetition rate: 10Hz, pulse duration ~5 ns, injection seeded) is used as the pump/probe for generating CARS/FWM signal. The frequency-doubled laser beam at $2\omega_p$($\lambda_2$=532 nm) pumps a tunable type II optical parametric oscillator 12 (Photop Technologies, OPO BBO-2B) to produce an idler beam at $\omega_s$ which is utilized as the Stokes beam for CARS holography, and a signal beam at $2\omega_p-\omega_s$ which is used as the reference beam for recording CARS holograms.

The pump/probe beam at $\omega_p$ passes through a variable delay line 14 and is focused by lens L1 (16) onto the sample 18. The Stokes beam is directed by mirror 20 and focused by lens L2 (22) onto the sample. A FWM signal is generated by the sample, in this example a CARS signal, and this passes through lens L3 (24), band pass filter F (26), and lens L4 (28), beamsplitter BS (30), before incidence on the imaging device 36. The reference beam is spatially filtered, polarization-rotated, and then directed by mirrors 32, 34 and pellicle beam splitter 30 onto the imaging device. Hence, the FWM signal and reference beam combine and form a holographic image on the imaging device.

The focal length of the lenses used were L1: singlet lens, focal length 750 mm, L2: singlet lens, focal length 150 mm, L3: long working distance objective lens, focal length 10 mm, L4: singlet lens, focal length 300 mm or 500 mm. The filter 26 selectively passes the FWM signal and removes the pump/probe and Stokes beam.

An advantage of the system is that the frequency of the reference beam automatically matches that of the CARS/FWM signal as the Stokes (or idler) wavelength is tuned using the OPO 12. The pump/probe and Stokes beams are focused onto the sample 18 (lens focal length: 750 mm and 150 mm respectively), and are spatially overlapped at the sample plane with an angle of about 20 degrees between them. Optimal temporal overlapping between the two beams can be obtained by tuning the delay line 14 in the pump/probe beam path.

A CARS/FWM image with a field of view diameter of about 120 μm was obtained. A small piece of Teflon was used to block the transmitted pump/probe and Stokes beams. The generated CARS/FWM image is then magnified by an imaging system comprising an objective (numerical aperture: 0.42, focal length: 10 mm) and a lens, filtered by a band-pass filter (ChromaD800/30), and detected by a CCD camera (Apogee 32ME).

To record a hologram, the reference beam first passes through a half wave plate to adjust its polarization (not shown in FIG. 1A). It is subsequently attenuated and spatially filtered (not shown in FIG. 1A) before combining with the CARS/FWM beam by using a pellicle beam splitter (reflectivity and transmittance ~8% and 92%, respectively) placed in front of the CCD camera. A delay line in the reference beam path (not shown in FIG. 1A) is adjusted to ensure optimal temporal overlapping between the CARS/FWM and reference pulses. After combining, the two beams propagate with a small angle between them and can interfere on the CCD camera to record a CARS/FWM hologram.

In other examples, an anti-Stokes beam may be used in place of the Stokes beam, allowing coherent Stokes Raman holography (CSRS holography).

Figure 1B:
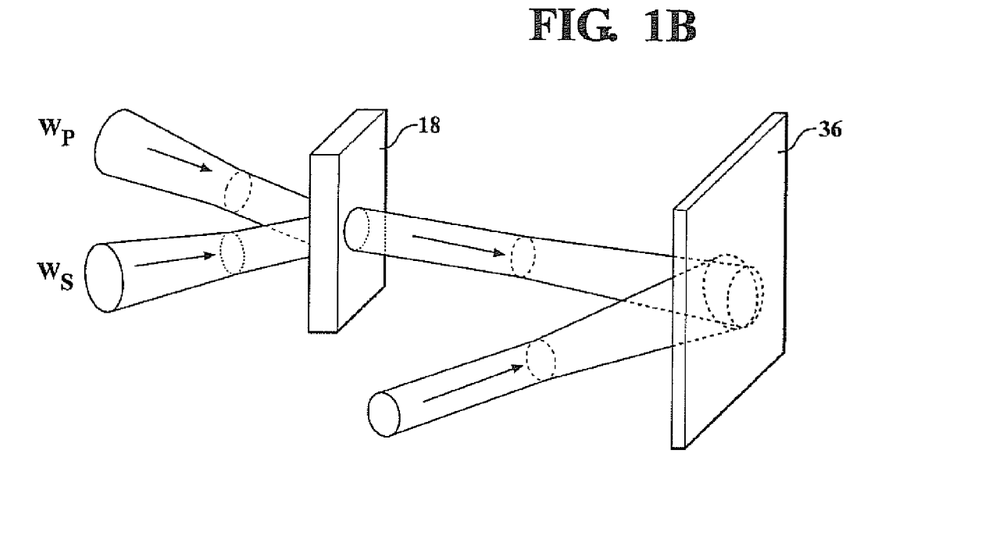
FIG. 1B shows a schematic diagram illustrating the principle of FWM holography, such as coherent anti-Stokes Raman (CARS) holography.

FIG. 1B illustrates the basic principle of FWM holographic imaging, in particular CARS holographic imaging. The pump/probe ($\omega_p$) and Stokes ($\omega_s$) beams are incident on the sample 18, generating the FWM signal, such as a CARS signal. A reference beam combines with the FWM signal to form a hologram at a holographic recording medium (imaging device) 36, such as an electronic imaging device. The imaging device may provide a hologram signal, such as an electronic image sensor signal, from which 2D and/or 3D images of the sample can be reconstructed.

Figure 1C:
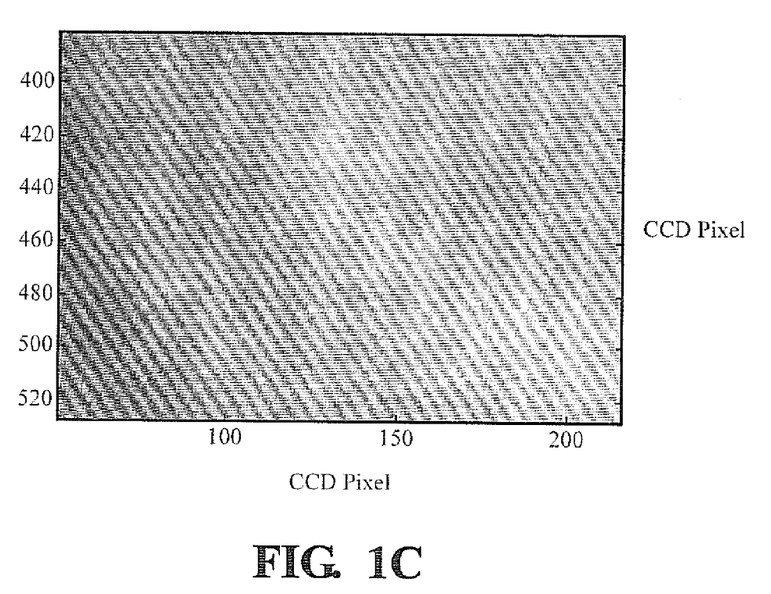
FIG. 1C is a typical hologram recorded on a CCD camera by interfering a single reference pulse and a signal pulse generated by FWM in index oil.

FIG. 1C shows a typical hologram recorded by interfering a single pair of reference pulse and FWM signal pulse generated from index oil. Interference fringes can be clearly observed. The period of the fringes is about 27 μm, consistent with an angle of approximately 1.7 degrees between the reference and the CARS/FWM beams.

The CARS signal generated from a polystyrene microsphere (Duke Scientific, nominal diameter: 10 μm) was obtained. The wavelength of the Stokes beam was tuned to resonantly excite molecular vibration (at around 3060 cm$^{-1}$) in the polystyrene sphere. The average energy of the pump/probe pulses was varied from 2 mJ to 7.5 mJ with an increment of 0.5 mJ each time while that of the Stokes pulses was fixed at about 4 mJ. The generated CARS signal strength was obtained by summing up the pixel values of the CARS signal captured on the CCD camera. An exposure time of 30 seconds was used during the measurement.

Figure 1D:
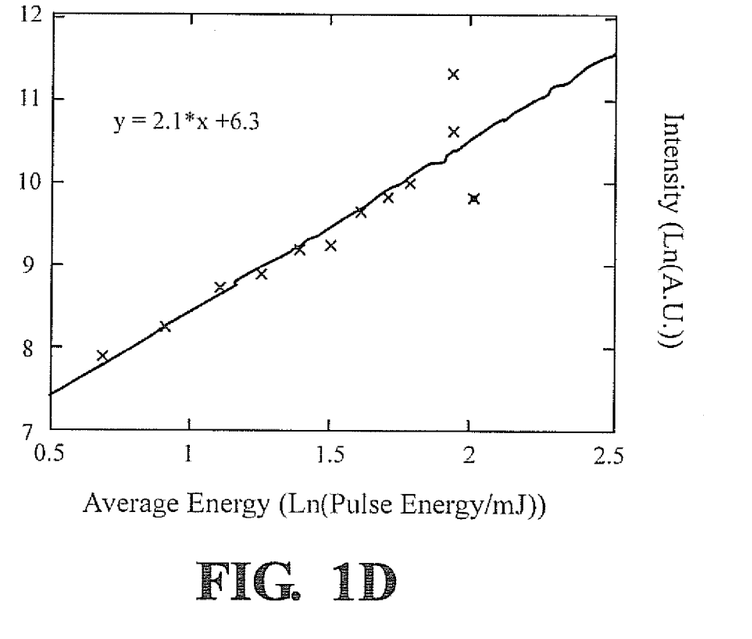
FIG. 1D shows the dependence of the CARS signal on the power of the pump/probe beam in a logarithmic scale.

FIG. 1D shows the dependence of the measured CARS signal strength on the average pulse energy of the pump/probe beam in logarithmic scale. The measured data can be fitted by a linear curve 50 with a slope of 2.1, indicating a quadratic relationship as expected. Deviation of the measured data from an ideal quadratic relationship is primarily caused by the shot-to-shot fluctuation of the optical parametric oscillator and the nanosecond laser and the limited accuracy in pulse energy measurement. This figure verifies the quadratic dependence of CARS signal on the power of the pump/probe beam.

Figure 2A:
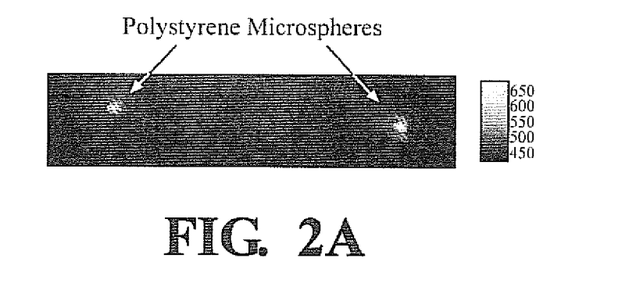
FIG. 2A is a single-shot CARS hologram recorded at polystyrene resonance wavelength.
Figure 2B:
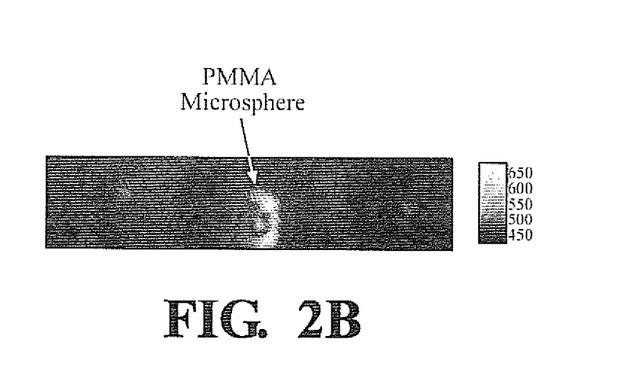
FIG. 2B is a single shot hologram recorded at PMMA resonance wavelength.

An advantage of CARS holography, as with CARS microscopy, is chemical selective imaging capability. To demonstrate this, a sample was prepared by sandwiching a PMMA microsphere (Bangs Lab., nominal diameter: 15 μm) and two polystyrene microspheres (Duke Scientific, nominal diameter: 10 μm) between a pair of microscope cover glasses (VWR No.1 cover glass). The microspheres were all immobilized on one of the cover glasses by using UV curable optical adhesive (Norland Optical Adhesive 60) and immersed in water. The edges of the cover glasses were sealed with silicone vacuum sealant. FIG. 2($a$) and (b) are the recorded CARS holograms when the Stokes wavelength was tuned to match the molecular vibrational frequencies of polystyrene and PMMA respectively. An exposure time of 90 ms was used to ensure single-shot recording as the repetition rate of the laser system was 10Hz.

FIG. 2A shows a recorded hologram obtained when the Stokes beam was tuned to the polystyrene resonance wavelength (corresponding to the Raman resonance at 3060 cm$^{-1}$). Strong CARS signal from the two polystyrene spheres can be observed in the recorded hologram). Only a weak non-resonant FWM signal was generated from the PMMA sphere in the middle.

FIG. 2B shows a recorded hologram obtained when the Stokes beam was tuned to the PMMA resonance wavelength (corresponding to the Raman resonance at 2959 cm$^{-1}$). Here, the situation was reversed. Strong CARS signal from the PMMA microsphere and weak non-resonant FWM signal from the polystyrene microspheres were recorded in the hologram. This clearly shows the unique chemical selective imaging capability of CARS holography.

The complex CARS field S can then be reconstructed by the following procedure. The two-dimensional (2D) Fourier transform of the recorded digital hologram is calculated; then one side band (e.g., corresponding to the term R*S) is selected through digital filtering; finally, the complex CARS image field can be obtained through the inverse 2D Fourier transform of the selected band. Three-dimensional CARS imaging can be achieved by digitally propagating the reconstructed complex CARS field. The digital propagation is realized by first taking the 2D Fourier transform of the complex field, then multiplying it by the transfer function[16] $e^{jk_zL}$ (where $k_z = \sqrt{(2\pi/\lambda)^2 - k_x^2 - k_y^2}$, $\lambda$ is the wavelength in the medium, ($k_x$, $k_y$, $k_z$) is the wave vector, and |L| is the propagation distance), and finally taking the inverse Fourier transform.

Figure 2C:
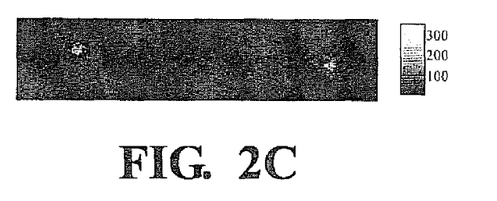
FIG. 2C is a reconstructed CARS intensity image from the hologram shown in FIG. 2A.
Figure 2D:
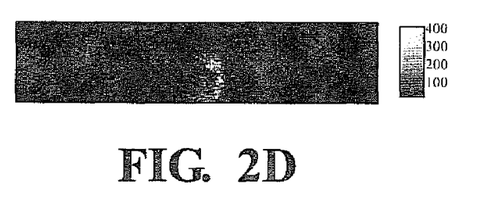
FIG. 2D is a reconstructed CARS intensity image from the hologram shown in FIG. 2B.

FIGS. 2C and 2D show the intensity of digitally reconstructed CARS images corresponding to the holograms shown in FIGS. 2A and 2B, respectively.

An advantage of CARS holography is that it captures both the amplitude and the phase of a CARS image and can therefore have 3D imaging capability. Consider a sample with a uniform refractive index and a relevant third order nonlinear susceptibility $\chi^{(3)}(x,y,z)$. The generated anti-Stokes field satisfies the following equation, $$\left[\nabla^2 + \frac{\omega^2}{c^2}n^2\right]E_{as} = -\frac{4\pi\omega^2}{c^2}\chi^{(3)}(x,y,z)E_p^2 E_s^*, \quad (1)$$

where $\omega$ is the angular frequency of the CARS signal, c is the speed of light in vacuum, and $E_p$ and $E_s$ are the pump/probe and Stokes fields. For simplicity, using scalar formalism assuming that the pump/probe and Stokes are un-depleted plane waves, i.e., $E_p = A_p e^{j\vec{k}_p \cdot \vec{r}}$ and $E_s = A_s e^{j\vec{k}_s \cdot \vec{r}}$ respectively, where $A_p$ and $A_s$ are the complex field amplitudes, $\vec{k}_p$ and $\vec{k}_s$ are the wave vectors.

By applying the slowly varying envelop approximation, the output anti-Stokes field $$E_{as}(x,y,L) = -\frac{4\pi\omega^2}{c^2}A_p^2 A_s^* e^{jk_{as}L} \quad (2)$$

$$\int_0^L dz e^{j\Delta kz}\left[\chi^{(3)}(x,y,z) * \frac{k_{as}}{j2\pi(L-z)}e^{j\frac{k_{as}}{2(L-z)}(x^2+y^2)}\right],$$

where L is the sample thickness, $k_{as}$ is the angular wavenumber of the generated anti-Stokes beam which propagates paraxially along the z axis, $\Delta k = 2k_{pz} - k_{sz} - k_{as}$, and "*" denotes two-dimensional (i.e., in x and y) convolution. The convolution kernel is actually the Fresnel diffraction kernel and the anti-Stokes field is proportional to the superposition of "diffracted" $\chi^{(3)}(x,y,z)$ at the output plane.

Three-dimensional CARS imaging can therefore be realized by digital propagation of the complex output anti-Stokes field which can be captured holographically. Other than a background term due to contributions from out-of-focus planes, the back-propagated field at z is approximately proportional to $\chi^{(3)}(x,y,z)$.

We experimentally investigated holographic CARS imaging of multiple polystyrene microspheres (nominal diameter: 10 μm) suspended in water. The sample was similarly prepared by sandwiching polystyrene microspheres (dispersed in water) between a pair of microscope cover glasses with the edges sealed by silicone vacuum sealant. In the experiment, the pulse energies of the pump/probe and Stokes were 8 mJ and 4 mJ respectively. The Stokes wavelength was tuned to the polystyrene resonance wavelength (i.e., Raman resonance at 3060 cm$^{-1}$). The CCD exposure time was set to 90 ms to ensure single shot recording.

Figure 3A:
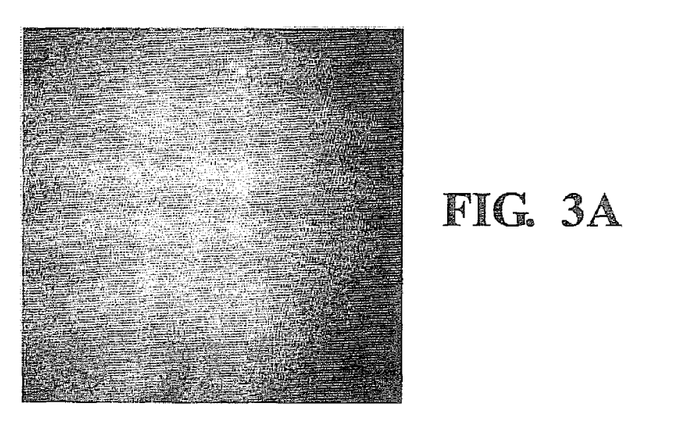
FIGS. 3A-3H illustrate three-dimensional CARS holographic imaging of polystyrene microspheres suspended in water.
Figure 3B:
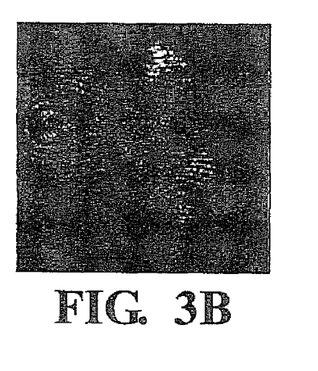
Figure 3C:
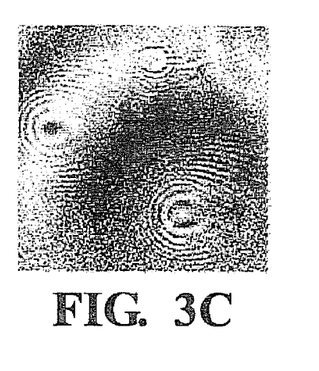
Figure 3D:
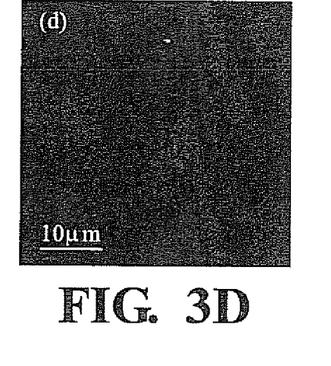

FIG. 3A shows a recorded CARS hologram. Interference fringes containing phase information can be observed. The reconstructed CARS intensity and phase image without diffraction compensation is shown in FIGS. 3B and 3C respectively. Three out-of-focus microspheres can be seen in the figures. Since the CARS hologram captures the complex CARS image field, it can be propagated digitally to realize 3D imaging as aforementioned.

Several field intensity distribution corresponding to different planes in the sample are shown in FIG. 3D-3G. Note that the intensity distributions of the digitally propagated CARS fields in FIGS. 3D and 3F have a much smaller spot size than that of the microspheres (diameter ~10 µm), indicating that the microspheres can actually focus the generated CARS field.

To confirm this lensing effect, we consider theoretically CARS generation in a single 10-µm-diameter microsphere (refractive index n=1.59) immersed in water (n=1.33). Both the pump/probe and Stokes beams are assumed to be undepleted and initially having Gaussian profiles with a propagation angle of 20° between them. The scalar wave equations governing the propagation of the pump/probe and Stokes beams and the generation of the anti-Stokes beam can be numerically solved by using the beam propagation method. Our simulation results show that the generated anti-Stokes beam is converging after exiting the microsphere.

Figure 3E:
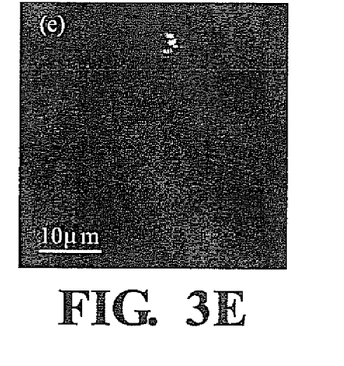
Figure 3F:
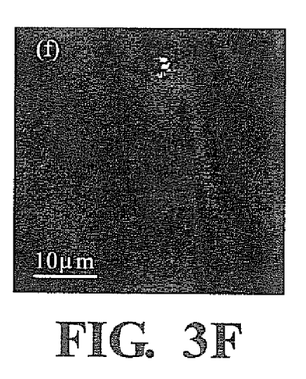
Figure 3G:
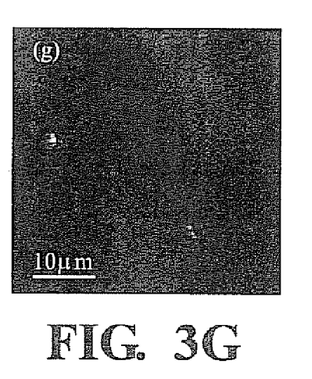
Figure 3H:
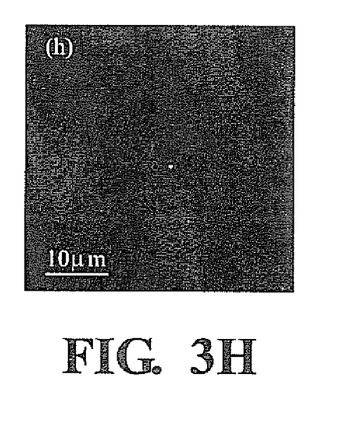

FIG. 3H shows the calculated intensity distribution of the generated anti-Stokes signal at a distance of 5 µm away from the exit plane, which is in good qualitative agreement with the experimental observation. The above analysis suggests that in order to obtain the CARS images of the microspheres, we need to continue the digital propagation for about 5 µm in addition until it reaches the exit plane of the microspheres. The results are shown in FIGS. 3E and 3G.

The results show that CARS images of polystyrene microspheres at different axial positions can all be digitally brought to focus. This indicates that CARS holographic imaging has a large depth of field and can therefore image a three dimensional scene. Some prior knowledge of the object itself is helpful in order to choose a proper digital propagation distance. An advantage of CARS holography is that this analogue "focus adjusting" process is replaced by digital propagation and as a result a 3D scene can be captured in a single exposure and later on reconstructed by "digital focusing." In general, a specimen would not always focus the generated anti-Stokes field and therefore a proper digital propagation distance can be usually chosen easily.

In-line Holography

Inline holographic coherent anti-Stokes Raman scattering (CARS) microscopy was implemented using a layer of uniform nonlinear medium placed in front of a specimen to be imaged. The reference wave created by four-wave mixing in the nonlinear medium can interfere with the CARS signal generated in the specimen to result in an inline hologram. Experimental and theoretical investigations of inline CARS holography show that it has chemical selectivity and allows three-dimensional imaging.

Figures 4A, 4B:
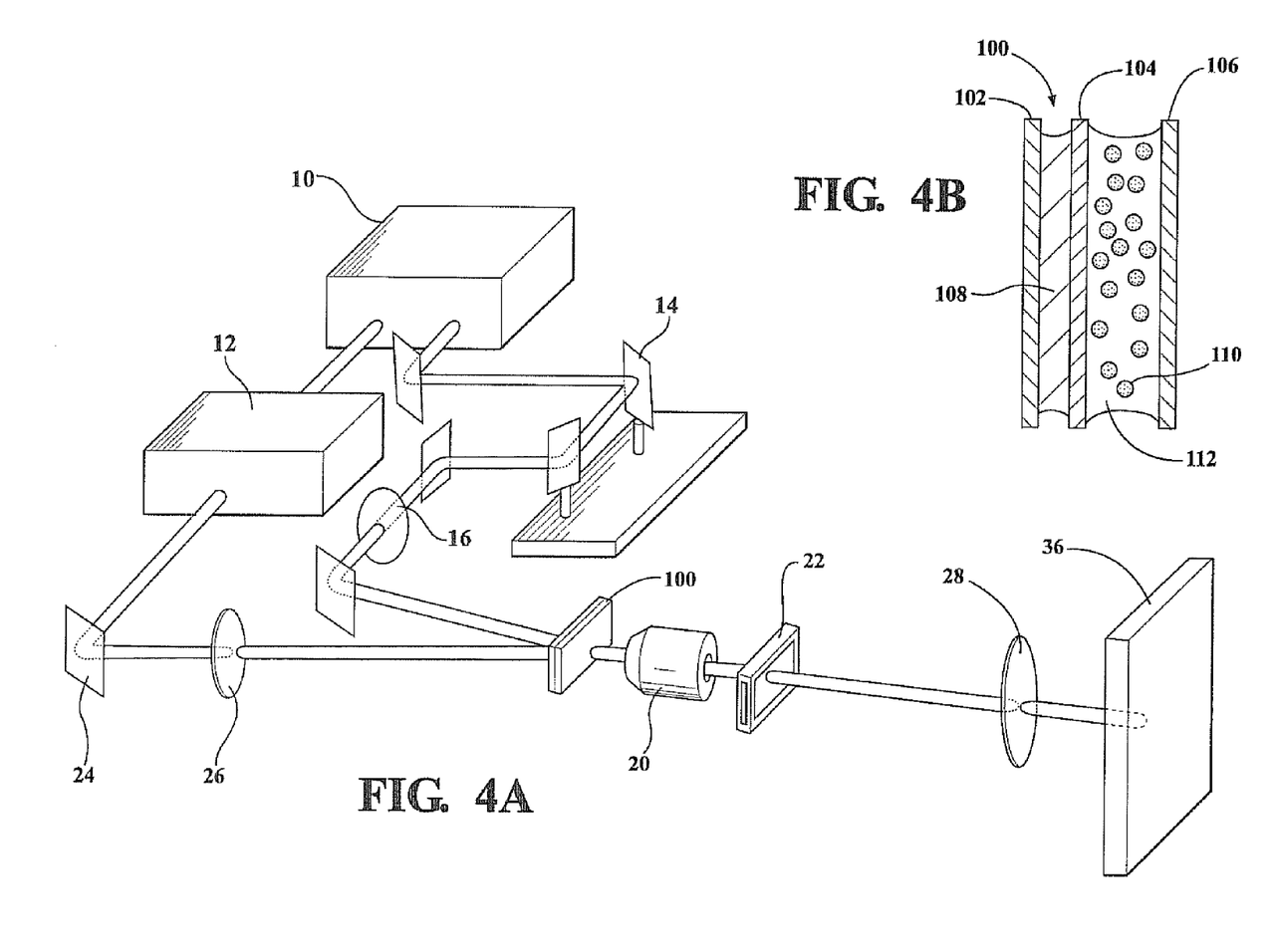
FIGS. 4A-4B illustrate an inline holography apparatus.

FIG. 4A shows a schematic diagram of an experimental setup. The figure shows a configuration similar to that shown in FIG. 1A, including laser 10, OPO 12, filter 22, imaging device 36, and lenses and mirrors as described in relation to FIG. 1A. In this configuration, the OPO receives frequency doubled radiation from the pulsed laser 10, and generates the Stokes beam. However, the reference beam is not generated by the OPO in this configuration. The sample holder 100 is configured to enclose the sample and a layer of nonlinear medium, as discussed further below in relation to FIG. 4B.

In the experimental configuration used, the output at fundamental frequency ($\lambda$=1064 nm) from the Q-switched pulsed laser (Continuum Surelite III, repetition rate: 10 Hz, pulse duration ~5 ns, injection seeded) is used as a pump beam for generating CARS signal. The frequency-doubled output from the laser is used to pump a type II optical parametric oscillator (OPO) (Photop Technologies, OPO BBO-2B) to produce a tunable Stokes beam.

The two beams are then weakly focused by two lenses with focal lengths of 750 mm and 150 mm respectively and spatially overlapped on the sample. A tunable delay line 14 in the pump beam path can be adjusted to optimize the temporal overlapping.

FIG. 4B shows the sample configuration 100 comprising two parts which are sandwiched between three glass slides, 102, 104, and 106 respectively. The first part 108 is a thin layer of uniform nonlinear medium, which is used to produce a reference beam through four wave mixing for recording the CARS hologram. In our experiments, index oil (about 10 µm thick) was used, but other materials can be used. The second part 112, which is placed behind the nonlinear medium, is the specimen to be holographically imaged, in this example including polymer microspheres 110. For other types of FWM holography, the nonlinear medium can be selected to generate the appropriate reference beam. The filter (F) is used to select the desired FWM wavelength, e.g. CARS, CSRS, and the like.

The CARS signal generated from the specimen interferes with the reference wave generated by the nonlinear medium. The resulted interference pattern (inline hologram) is magnified by an imaging system consisting of a long-working-distance objective lens 20 (in this experiment, having a numerical aperture 0.42, and focal length 10 mm) and a lens 28 (focal length 500 mm), and captured by the imaging device 36, a CCD camera (Apogee 32111E). The undepleted pump and Stokes beams are blocked with a small piece of Teflon. The band-pass filter (Chroma D800/30) is used to further filter out any remaining pump and Stokes beams.

The experimental specimen comprised a poly(methyl methacrylate) (PMMA, Bangs Lab., nominal diameter: 10 µm) and a polystyrene (Duke Scientific, nominal diameter: 10 µm) microsphere immobilized on a cover glass (VWR No.1 cover glass) by UV curable optical adhesive (Norland Optical Adhesive 60). The whole sample was sandwiched between three pieces of cover glass. Index oil was sealed between the first two cover glasses while the third glass was the one with immobilized microspheres which were immersed in water. Silicone lubricant was used to seal the edges of the glasses to avoid leakage.

Figure 5A:
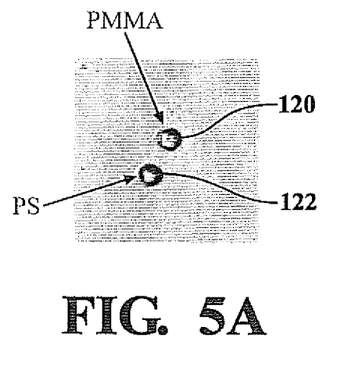
FIG. 5A shows an optical microscope image of a PMMA and a polystyrene (PS) spheres.
Figure 5B:
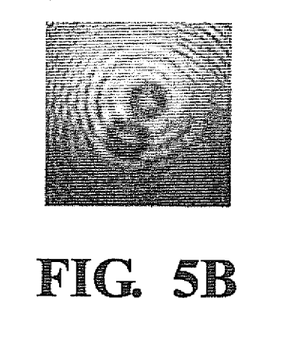
FIG. 5B shows a hologram recorded at PMMA resonance.
Figure 5C:
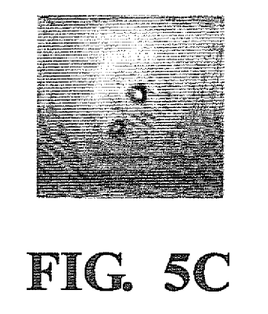
FIG. 5C shows reconstruction by digital back-propagation showing a resonant PMMA microsphere.
Figure 5D:
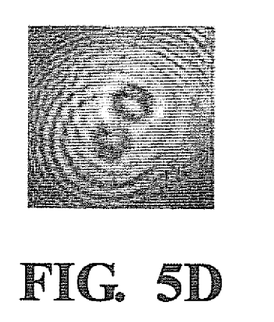
FIG. 5D shows a hologram recorded at polystyrene (PS) resonance.
Figure 5E:
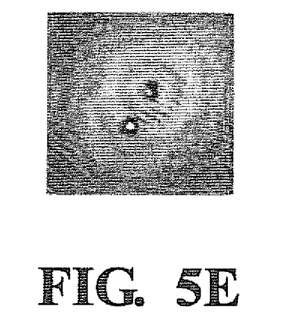
FIG. 5E shows reconstruction by digital back-propagation showing a resonant PS microsphere.
Figure 5F:
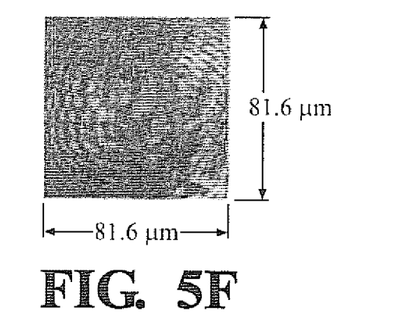
FIG. 5F shows a hologram recorded without the use of a nonlinear layer.

FIGS. 5A-5F show chemical selective in-line holographic CARS imaging using inline holography, where FIG. 5A shows an optical microscope image of a PMMA and a polystyrene (PS) spheres; FIG. 5B shows a hologram recorded at PMMA resonance; FIG. 5C shows reconstruction by digital back-propagation showing a resonant PMMA microsphere; FIG. 5D shows a hologram recorded at polystyrene (PS) resonance; FIG. 5E shows reconstruction by digital back-propagation showing a resonant PS microsphere; and FIG. 5F shows a hologram recorded without the use of a nonlinear layer.

Inline holograms of the specimen were obtained using the apparatus of FIGS. 4A-4B. The energies of the pump pulse and Stokes pulse were about 8 mJ and 4 mJ, corresponding to peak intensities of approximately 5 GW/cm$^2$ and 16 GW/cm$^2$ respectively. The exposure time was 1.5 seconds corresponding to about 15 shots of pulsed exposure. The Stokes beam was first tuned to resonantly excite the vibrational mode of PMMA at 2959 cm$^{-1}$.

FIG. 5B shows a hologram recorded at PMMA resonance. The specimen was defocused during the recording. The hologram was then digitally back-propagated and the reconstruction is shown in FIG. 5C. We can clearly see that the PMMA sphere is much brighter than the polystyrene sphere.

However, the off-resonant polystyrene sphere is also observable and shows focusing/defocusing effect as well during digital back-propagation. This might originate from two reasons: first, the non-resonant four waving mixing background generated by the off-resonance sphere can interfere with the reference wave to record a weak four wave mixing hologram; second, the scattering of the reference wave by the polystyrene microsphere can also result in a Gabor hologram. In order to record a high quality CARS hologram, the contributions due to both non-resonant four wave mixing background and scattering of the reference wave need to be suppressed.

FIG. 5D shows a hologram obtained at polystyrene resonance. The wavelength of the Stokes beam was tuned to resonantly excite the vibrational mode of polystyrene at 3060 cm$^{-1}$, using the same exposure time and excitation pulse energies.

FIG. 5E shows the digital back-propagation result which reveals that the polystyrene microsphere is much brighter than the PMMA sphere in this case. This shows that inline holograms with good chemical selectivity can be obtained by our system.

Nonresonant four wave mixing background can also be generated from any surrounding medium (e.g., water, in the experimental example) as well as glass cover slides and could be used to obtain a reference wave for recording inline holograms. Under our experimental conditions, the nonresonant background was not strong enough for recording holograms of good quality.

FIG. 5F shows a hologram recorded without the use of a nonlinear layer. As can be seen, the fringes are hardly visible.

Inline holographic imaging was obtained of multiple PMMA microspheres suspended in water. During the experiment, the Stokes wavelength was tuned to match PMMA resonance at 2959 cm$^{-1}$. The energies of pump and Stokes pulses were about 10 mJ and 5 mJ, corresponding to peak intensities of approximately 6 GW/cm$^2$ and 20 GW/cm$^2$ respectively. The exposure time was set to 90 ms to ensure single shot exposure. The microspheres were essentially still during the recording as the pulse width of the laser is only about 5 ns. In-line CARS holograms were obtained of PMMA microspheres suspended in water, and digital back-propagation was used to obtain images at different planes within the sample. Hence, an improved FWM holography method includes adjusting the image analysis parameters to generate images corresponding to different planes of the sample.

Advanced signal processing techniques, such as compressive holography (Optics Express, 17, pp. 13040-13049, 2009, Optics Express 18, pp. 8213-8219, 2010), can be applied to inline CARS holograms to improve the reconstruction.

The recording of inline CARS holograms is discussed theoretically below. Under scalar and undepleted pump and Stokes approximation, the anti-Stokes, the pump, and the Stokes fields satisfy the following wave equations respectively.

$$\left[\nabla^2 + \frac{\omega_{as}^2}{c^2} n(\omega_{as}, x, y, z)^2\right] E_{as} = -\frac{4\pi \omega_{as}^2}{c^2} \chi^{(3)} E_p^2 E_s^* \quad (3)$$

$$\left[\nabla^2 + \frac{\omega_p^2}{c^2} n(\omega_p, x, y, z)^2\right] E_p = 0 \quad (4)$$

$$\left[\nabla^2 + \frac{\omega_s^2}{c^2} n(\omega_s, x, y, z)^2\right] E_s = 0 \quad (5)$$

where $\omega_{as}$, $\omega_p$, $\omega_s$ are the angular frequencies of the anti-Stokes, pump, and Stokes beams, c is the speed of light in vacuum, n is the refractive index of the specimen, $\chi^{(3)}$ is the relevant third order nonlinear susceptibility, and $E_{as}$, $E_p$ and $E_s$ are the anti-Stokes, pump and Stokes fields in the specimen. Assuming small variation of the refractive index, Eq. (3) can be rewritten as:

$$\left(\nabla^2 + \frac{\omega_{as}^2}{c^2} \bar{n}^2\right) E_{as} = -\frac{4\pi \omega_{as}^2}{c^2} \chi^{(3)} E_p^2 E_s^* - \frac{\omega_{as}^2}{c^2} 2\bar{n} \Delta n E_{as} \quad (6)$$

where $\bar{n}$ is the average refractive index and $\Delta n = n - \bar{n}$ is the index variation. The second term on the right hand side of Eq. (6) represents the scattering effect due to a non-uniform linear refractive index distribution. If the specimen is linear, i.e., $\chi^{(3)} = 0$, Eq. (6) describes the scattering of the reference wave and can be rewritten by using Born's approximation:

$$\left(\nabla^2 + \frac{\omega_{as}^2}{c^2} \bar{n}^2\right) E_{sc} = -\frac{\omega_{as}^2}{c^2} 2\bar{n} \Delta n E_r \quad (7)$$

where $E_r$ denotes the reference wave created by four wave mixing in the nonlinear medium placed in front of the specimen, and $E_{sc}$ is the scattered field. This equation can be solved by using the Green's function. The total field is then given by $E_r + E_{sc}$. As a result, a Gabor hologram can be recorded by capturing the total intensity $|E_r + E_{sc}|^2$. In general, Eq. (6) is solved numerically and the solution includes both the contribution due to scattering of the reference wave and the anti-Stokes signal generated in the specimen. The recorded intensity distribution is therefore given by $I \propto |E_r + E_{sc} + E_{as}^s|^2$ where $E_{as}^s$ is the anti-Stokes field of interest generated by the specimen.

To obtain a genuine CARS hologram, the contribution due to the scattered field needs to be suppressed (i.e., $|E_{sc}| \ll |E_{as}^s|$), since it lacks chemical selectivity. Therefore, weak scatterers and/or a relatively weak reference wave are preferred.

A modeled sample comprised a 10 μm thick nonlinear medium with nonlinear susceptibility $\chi_{NM}^{(3)}$, a 160 μm thick spacer, and a specimen consisting of two 10-μm-diameter microspheres A and B immersed in water with identical refractive index of 1.5 and separated by about 14 μm. Further, we assume that microsphere A is on resonance and the ratio of the corresponding third order nonlinear susceptibilities is given by $\chi_{NM}^{(3)} : \chi_A^{(3)} : \chi_B^{(3)} = 1.2 : 1 + j : 1$.

As aforementioned under our experimental conditions the nonresonant background generated from surrounding medium and glass cover slides are quite weak for recording holograms. For modeling simplicity, both the spacer and water are assumed to be linear (i.e. $\chi^{(3)} = 0$) in our model. Eq. (3)-(5) can be solved using the beam propagation method. The initial pump and Stokes fields were assumed as Gaussian beams. Reconstruction by digital back-propagation of the theoretical inline hologram qualitatively agreed with the experimental results. Simulations also showed that the generated CARS field is focused by the microsphere, which therefore results in a bright spot much smaller than the size of the sphere itself.

Inline CARS holography has good chemical selectivity and three-dimensional imaging can be achieved by digitally propagating the hologram. Compressive holography techniques can be used reconstruct the recorded inline hologram, allowing significantly suppression of the twin image background.

A scattered reference may lead to a superposition of inline CARS hologram with Gabor hologram, and reducing the chemical selectivity. The scattered field may interfere destructively or constructively with the CARS signal generated in the specimen to result in non-uniform image intensity. In addition, the scattered field could also interfere constructively with nonresonant four wave mixing background by lucky phase matching while interfering destructively with resonant CARS signals generated at certain locations, which can potentially result in enhanced background and difficulty in interpreting the results. If necessary, these limitations can be overcome by generating the reference wave of axis to avoid its propagation through the specimen and hence the recording of a Gabor hologram.

Inline CARS holography is simple to implement and is relatively robust against system instability due to the fact that both the reference and signal can be generated by the same pump and Stokes beams and co-propagate in the same media. It can be a very useful technique for relatively thin samples (compared to the coherence length of CARS processes), or when combined with other techniques which can suppress the nonresonant background.

Examples of the present invention include both in-line and off-axis FWM holography. In in-line holography, the FWM (e.g. CARS) signal is generally coaxial with the reference beam. In off-axis holography, the FWM signal and the reference beam are non-parallel, and converge on the imaging device. In some examples, a FWM signal generated by the pump/probe and Stokes from a nonlinear medium (e.g., a thin layer of index oil) is used as a reference beam. In some examples, FWM is generated by nonlinear wave mixing of multiple beams (e.g., pump/probe and a Stokes beam) and the reference with a matched frequency to the FWM is generated from a nonlinear medium.

Inline holography may be implemented with the CARS beam (or other FWM signal) and reference beam propagating co-linearly rather than at an angle to each other. This can be realized in a simple geometry (e.g. just stacking the nonlinear medium with a sample). Example inline holography methods and apparatus include stacking a nonlinear medium (to generate a CARS reference beam) with a sample to be imaged. FWM holography apparatus, such as CARS holography apparatus, may include both in-line and off-axis realizations, which are different in reconstruction.

Multiplex FWM/CARS Holography

A multiplex FWM (e.g. CARS) holographic imaging technique is described, which can simultaneously image multiple molecular species in three dimensions without scanning. Briefly, multiple molecular vibrational modes (i.e., modes of different molecules, or different modes of the same molecule) are first excited by a pump beam and a broadband Stokes beam, or impulsively by a single broadband beam (e.g., a supercontinuum beam). A multiplex hologram includes holograms at a plurality of spatial carrier frequencies, which can be collected simultaneously, in some examples using a single laser pulse.

A probe beam then interacts with the vibrating molecules to create a multiplex CARS image containing multiple molecular vibrational signatures. A reference beam with multiple matched wavelengths then interferes with the CARS image to create a multiplex CARS hologram. Note that the different wavelengths of the reference beam can have identical (i.e., wavelength-multiplexed hologram), or different (wavelength-and-angle-multiplexed hologram) propagation directions that can be accomplished by passing the broadband reference beam through a dispersive element such as a grating or a prism. The multiplex CARS hologram can be de-multiplexed due to the fact that the sub-holograms corresponding to different molecular vibrational mode have different carrier frequencies and can therefore be separated in the spatial frequency domain.

Complex images by utilizing different vibrational mode to provide contrast can then be reconstructed individually, leading to simultaneous three-dimensional chemically selective imaging of multiple molecular species.

The multiplex CARS holography is a special case of the more general multiplex FWM holography, in which a broadband FWM signal interferes with a broadband reference wave to record a multiplex hologram. The FWM processes include but are not limited to coherent Stokes Raman scattering, stimulated Raman scattering, four wave mixing due to electronic responses, and Brillouin scattering.

Figure 6A:
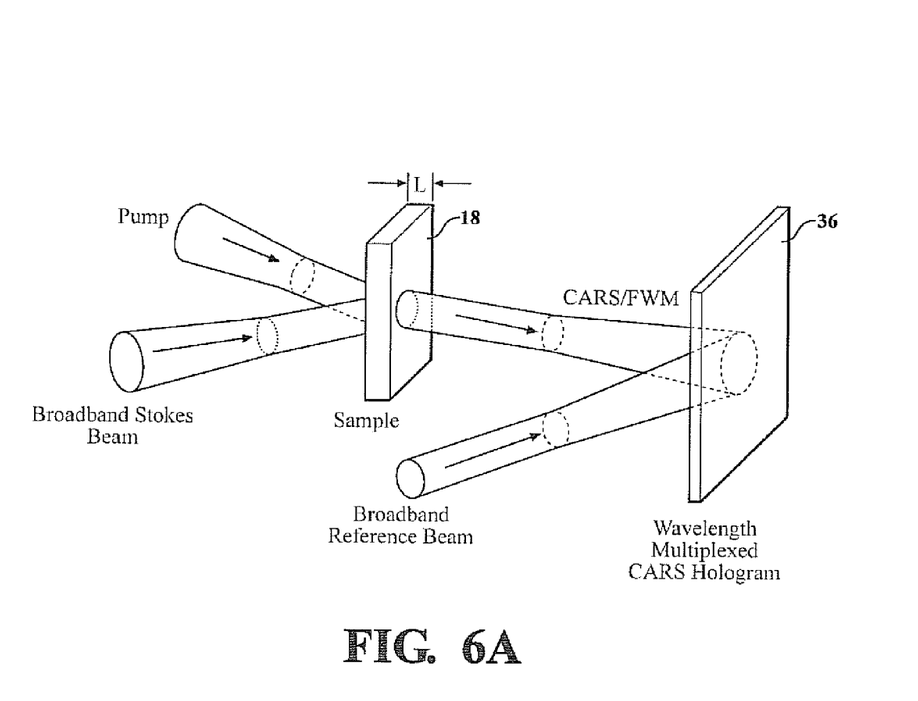
FIGS. 6A-6B illustrate multiplex FWM/CARS holography.

FIG. 6A shows the schematic diagram of an exemplary implementation of the multiplex FWM/CARS holography. A broadband Stokes beam is used in conjunction with a pump beam to generate a broadband multiplex FWM/CARS image of the sample 18. A broadband reference beam (e.g., a properly filtered supercontinuum) containing wavelengths matched to those in the FWM/CARS signal can then be used to record a wavelength-multiplexed FWM/CARS hologram at the imaging device 36.

Figure 6B:
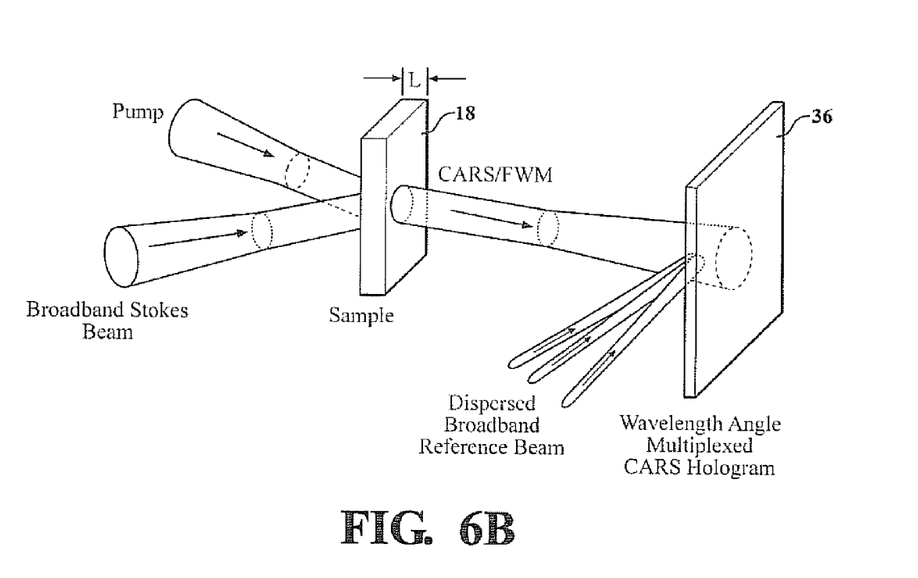

FIG. 6B shows another possible implementation. Here the different wavelength components of the reference beam are first dispersed by a dispersive element such as a grating or a prism so that they propagate at different directions. As a result, they interfere with the corresponding wavelength components of the CARS/FWM signal at different angles. In both examples, the resulting hologram of the sample 18 contains multiplexed sub-holograms with different spatial carrier frequencies due to the different recording wavelengths and/or the different recording angles, which can be separated in the spatial frequency domain and individually reconstructed.

Using multiplex FWM holography allows simultaneous formation of a plurality of FWM holograms having differing spatial carrier frequencies. A hologram signal from an electronic image sensor then captures the plurality of holograms, and an image can be obtained for a specific spatial carrier frequency using signal processing. For example, the holographic signal can be 2D-Fourier-transformed; different holograms having different spatial carrier frequencies (or different spatial periodicities) can then be separated from each other in the Fourier domain if the carrier frequency differences are sufficiently large; a particular hologram can then be selected through digital filtering.

Multiplex FWM/CARS holography allows simultaneous imaging of e.g. different molecular species within the sample. This can be achieved using a single pump-probe pulse.

In some examples, vibrational transitions may be too close to allow acceptable separation of holographic image data. As the vibrational frequencies become closer, the spatial periodicities of the corresponding holograms also becomes closer and there may be cross-talk between signals. However, using the dispersive approach shown in FIG. 6B, the spatial periodicity differences can be enhanced, facilitating the imaging of close vibrational transitions within the sample. A dispersive element within the reference beam enhances the spatial periodicity differences of different holograms.

A broadband beam may be a supercontinuum beam, which may be spectrally filtered to image a desired spectral range of vibrational transitions. For example, a broadband beam may have a bandwidth of 50 nm-1,500 nm, such as 100 nm-1000 nm, for example a wavelength range from 800 nm to 1200 nm. However, these examples are illustrative and not limiting. A broadband beam may have a bandwidth of at least 50 nm, for example at least 100 nm. The different vibrational transitions encoded within multiplexed holographic data can be studied individually by modifying the signal processing of the holographic data.

In other examples, at least one of the first, second, and third beams (e.g. the Stokes beam) and the reference beam may include a number of discrete frequencies. For example, the FWM signal and reference beam may include a plurality of matched frequencies, allowing simultaneous formation of holograms at these discrete frequencies. Multiplex holograms can be formed using supercontinuum, spectrally filtered, or discrete wavelength radiation sources.

Applications

Coherent anti-Stokes Raman holographic imaging was experimentally demonstrated, combining the capabilities of both CARS and holography. By capturing both the amplitude and the phase of a complex CARS image field, CARS holography can have a large depth of field and therefore chemical-selectively image a three-dimensional object without scanning. Examples of the present invention include improved imaging apparatus, such as holographic CARS microscopes and other imaging devices.

Examples further include apparatus and methods for other FWM holographic imaging. Any example apparatus or method described for CARS, as a representative example, may also be adapted for use with one or more other FWM holographic approaches.

Imaging applications include imaging of samples such as nanostructures, microstructures, and the like. Imaged samples may include biological structures, such as cells, biomolecules (such as proteins, enzymes, DNA, and the like), other macromolecules (such as polymers), and any other structures of interest.

Time-dependent image data can be collected, allowing 4D imaging (3 spatial dimensions and time). Examples include imaging of biological processes, such as studying protein folding, enzyme activity, molecular recognition processes, genome interactions, and other biological interactions and processes.

Some examples include study of chemical processes, such as study of reaction dynamics, equilibrium changes, isomerization (including stereoisomerism), and the like. Examples also include the study of physical and/or chemical effects within a sample, such as thermal processes, optically induced processes, and the like.

Some examples also include the imaging of fabricated nanostructures. Examples also include analytical instruments including nanostructures or microstructures, such as microfluidic devices, and the like.

Example applications include multifunctional imaging apparatus combining a CARS imaging capability with other imaging functions, such as optical, IR, fluorescence, other linear and/or nonlinear imaging capabilities.

Unlike several other imaging techniques, it is not necessary to introduce labels (such as fluorescent labels) into the sample. Samples may be imaged directly, without introducing extra materials such as optical labels. However, in some examples a Raman active material may be introduced into a sample as a label, and the sample imaged by imaging CARS from the Raman active material.

Wavelength Tuning

In an example approach, such as illustrated in FIG. 1B, a sample is illuminated by a pump/probe beam (having a pump/probe frequency, $\omega_p$) and a Stokes beam (having a Stokes frequency $\omega_s$). A CARS signal generated (having CARS frequency $2\omega_p-\omega_s$) is then combined with a reference beam to produce a CARS hologram. In this configuration, the pump and probe beam are provided by the same source, such as a pulsed laser. In other examples, the pump and probe beam may have different frequencies, e.g. $\omega_p$ and $\omega_p'$ respectively so that the CARS frequency is $\omega_p+\omega_p'-\omega_s$ and/or different propagation directions. Molecular vibrational frequencies can be determined from the difference between the pump/probe beam and the Stokes beam. (In this example, CARS is considered, but other FWM signals may be generated using appropriate wavelength relationships.)

The Stokes beam and a reference beam at the CARS frequency can be generated together using an optical parametric oscillator (OPO). In an example approach, the output of a pulsed laser is used as the pump/probe beam, and frequency doubled radiation from the laser is used as the input to an OPO. The OPO gives two output beams (sometimes referred to as signal and idler beams), a first beam at a first frequency, and a second beam at a second frequency that is the difference between the first frequency and the input frequency. If the first frequency is the Stokes frequency, then the second frequency is double the pump/probe beam minus the Stokes frequency, i.e. the same as the CARS frequency. The first OPO beam is used as the Stokes beam, and the second OPO beam is used as the reference beam. This configuration has several advantages, for example generating all required beams from one radiation source, and a simple approach to tuning that facilitates collection of vibrational spectra.

Tuning the OPO allows the Stokes beam and reference beam to be tuned together, allowing different vibrational frequencies to be studied while retaining the relationship (for example, equality) to be maintained between the reference beam and the CARS signal frequency.

In other examples, the reference beam can be generated having frequency $2\omega_p-\omega_s$ (twice the pump/probe beam frequency minus the Stokes frequency) using any appropriate nonlinear element(s), which need not be an OPO, even if the Stokes beam is provided by a separate tunable source from the pump/probe beam, or generated from the same source of pump/probe radiation using any method.

Other Aspects

Examples of the present invention include four wave mixing holography, where the FWM signal is generated by any process (including CARS, CSRS or other related Raman holography such as stimulated Raman holography, and the like).

CSRS (coherent Stokes Raman scattering) can be studied with a slight modification to the CARS holography apparatus discussed earlier in relation to FIG. 1. CSRS holography can be achieved by generating the CSRS signal using the pump/probe and reference beams (as used to record CARS hologram in CARS holography), and then combining the CSRS signal with the Stokes beam (now used as the reference beam to record the CSRS hologram).

For example, for CSRS holography, an apparatus similar to that of FIG. 1B can be used, except that Stokes beam for CARS becomes the anti-Stokes beam for CSRS, and CARS FWM signal becomes a CSRS FWM signal for CSRS holography. In general, we can interchange Stokes with anti-Stokes beams to achieve CSRS holography. The anti-Stokes beam (which is used as the reference beam in CARS) is used to generate the CSRS signal while the Stokes beam (which is used to generate CARS) is used as reference for CSRS holography.

Similar approaches can be used for other Raman processes (such as stimulated Raman scattering, CSRS, resonance Raman, surface-enhanced Raman scattering (SERS), and other nonlinear or linear vibrational spectroscopies.

In other examples, the beam referred to as the Stokes beam may not be at the correct frequency to excite molecular vibration (i.e. $\omega_p - \omega_s \neq \omega_{vibrational}$), or the sample may not be Raman active. However, the term Stokes beam may still be used for convenience, though the collected image data may be more correctly referred to as four-wave mixing holography. Similar apparatus and methods can be used to for other four-wave mixing holography, and other nonlinear wave mixing imaging.

A CARS holography system, such as described above, can be readily modified and used for CSRS holography by generating the CSRS signal using a pump/probe beam and the beam used as the "reference" to record CARS hologram in CARS holography, and then combining the CSRS signal with the beam used as the "Stokes" beam in the CARS system, which is used as the reference to record a CSRS hologram.

In other words, the reference beam of the CARS system may be used as the anti-Stokes beam of a CSRS system, and the Stokes beam of the CARS system may used as the reference beam in the CSRS system. An example apparatus or method includes interchanging the reference and Stokes beams to study both CARS and CSRS holography.

A pump/probe beam and a tunable Stokes beam with respective angular frequencies $\omega_p$ and $\omega_s$ interact with a sample to produce four wave mixing (FWM) signal, such as a resonant CARS signal if the frequency difference between the pump and the Stokes ($\omega_p - \omega_s$) matches the molecular vibrational frequency of the sample. A reference beam $Re^{-j(2\omega_p - \omega_s)t}$ with angular frequency $2\omega_p - \omega_s$ then interferes with the generated FWM image $Se^{-j(2\omega_p - \omega_s)t}$ to record a CARS/FWM hologram $|R+S|^2$, from which the complex FWM field S can be reconstructed.

Examples of the present invention include four wave mixing holography in which a sample is illuminated with at least two beams (a pump-probe beam, which may be a single beam or separate pump and probe beams, and a "third beam", corresponding to the Stokes beam in CARS. The FWM signal (the CARS signal in the case of CARS holography) is then combined with a reference beam so as to form a hologram. The "third beam" and the reference beam may be generated in the same way as the Stokes beam and the reference beam in the CARS approach.

Other examples include Brillouin scattering holography, which can be used to image mechanical properties, as another example of FWM holography.

Data Collection and Analysis

An apparatus can be used to collect spectral data, for example a vibrational spectrum. In some cases, a Stokes frequency is selected that gives a good image of the sample, and spectral data need not be collected. In some cases, a discrete number of Stokes frequencies are used to monitor conversion from a first state to a second state.

The holographic information can be recovered from data collected from an electronic image sensor using computational methods. A hologram can be formed in a photographic film or other imaging medium; FWM/CARS holography methods and apparatus include both in-line and off-axis realization, e.g. relating to the relative orientation of FWM signals and reference beam.

An example apparatus includes a laser (pulsed laser or CW laser, or other radiation source) generating the pump/probe beam, a frequency doubler generating a doubled frequency beam, and an OPO (or other nonlinear optical device) receiving the doubled frequency beam and generating both the Stokes beam and the reference beam. The Stokes beam and the pump/probe beam are both incident on the sample, and the CARS radiation is collected and combined with the reference beam on an imaging device, such as an electronic image sensor, to allow the holographic information to be collected.

Using a pulsed laser, an image may be generated using a single pulse of the pump-probe beam. Multiple pulses can be used to improve an image. For dynamic studies, one pulse, some number of pulses, or a predetermined time of CW illumination can be used, time periods or number of pulses being determined by time resolution required. Time resolution may be changed as desired. A dynamic process can be tracked using a plurality of single pulse images.

Wavelengths of the pump, probe, Stokes, and reference can be adjusted depending on the target analyte, and to obtain spectral information. Lasers, OPOs, or other components may be tuned, filters adjusted, and the like. Vibrational spectral information can be obtained by tuning the Stokes beam.

Hence, CARS holography can capture at a single shot (illumination pulse) both the amplitude and phase of a coherent Raman image. It allows non-scanning chemically selective 3D imaging at a speed only limited by the laser pulse width, which is not possible using any existing laser scanning based Raman imaging methods. Single-shot (~5 ns) three-dimensional holographic Raman imaging of microspheres was demonstrated. In some examples, the laser pulse duration may be in the range 1 ps-1000 ns, for example 1 ps-100 ns. Multiple illumination pulses may be used to increase signal-to-noise, but 3D imaging is possible using a single laser pulse. For example, pump/probe, Stokes, and reference beam pulses may be generated from a single laser pulse from the radiation source, and used to obtain a FWM hologram.

Experimental results show that coherent anti-Stokes Raman holography is a new, useful method for chemically selective 3D imaging of fast phenomena, such as processes occurring on time scales of microsecond, nanoseconds, or picoseconds. Examples of the invention include new non-scanning 3D Raman imaging apparatus. Examples of the invention include bio-medical imaging and microscopy, including ultra-fast imaging (imaging in less than 100 ns, in some cases less than 10 ns, such as ~5 ns), and 3D Raman imaging without scanning.

Holograms can be recorded with multiple shots for improved signal strength. Laser beams used can be pulsed lasers, and can also be a continuous wave beam with high enough intensity.

Patents or other publications mentioned in this specification are herein incorporated by reference to the same extent as if each individual publication was specifically and individually indicated to be incorporated by reference.

The invention is not restricted to the illustrative examples described above. Examples are not intended to limit the scope of the invention. Changes therein, other combinations of elements, and other uses will occur to those skilled in the art. The scope of the invention is defined by the scope of the claims.

Having described our invention, we claim:

1. An apparatus, the apparatus being a four-wave mixing (FWM) holography apparatus for characterizing a sample, the apparatus comprising:
a sample illumination system comprising a pulsed or continuous wave laser, said laser configured to generate a first beam, said system further generating a second beam from said laser or a second laser;
a third beam generator comprising a radiation source, said third beam generator providing a third beam;
a sample electromagnetically associated with said first beam and said third beam wherein a frequency difference between said first beam and said third beam matches a resonant frequency of the sample so as to generate a four-wave mixing (FWM) signal from the sample;
a reference beam and the FWM signal combining to form a FWM hologram; and
an imaging device, the imaging device capturing the FWM hologram.

2. The apparatus of claim 1, the first beam and the second beam being provided by a single pump-probe beam from a single laser,
the third beam being a Stokes beam or an anti-Stokes beam.

3. The apparatus of claim 1, the apparatus being a coherent anti-Stokes Raman scattering (CARS) holography apparatus,
the FWM signal being a CARS signal, and
the third beam being a Stokes beam.

4. The apparatus of claim 3, wherein said third beam generator is an optical parametric oscillator
configured to generate both the Stokes beam and the reference beam,
the OPO being tunable so as to adjust the frequencies of both the Stokes beam and the reference beam simultaneously,
the reference beam remaining frequency matched to the CARS signal as the OPO is tuned.

5. The apparatus of claim 1 further comprising a layer of nonlinear material adjacent the sample, the reference beam being generated by said layer of nonlinear material.

6. The apparatus of claim 1, the reference beam and at least one of the first, second, and third beams being broadband beams, so as to generate a plurality of FWM holograms having different spatial carrier frequencies.

7. The apparatus of claim 6, the apparatus further including a signal analyzer, the hologram carrier frequency being selectable by the signal analyzer to form an image of a selected FWM process within the sample.

8. The apparatus of claim 1, the imaging device being an electronic imaging device,
the apparatus further including a signal analyzer operable to receive a hologram signal from the electronic imaging device and to create an image of the sample from the hologram signal using signal processing.

9. The apparatus of claim 8, the image corresponding to an image plane within the sample, the image plane location being adjustable by adjustment of a signal processing parameter.

10. The apparatus of claim 8, the image corresponding to a FWM hologram frequency, the FWM hologram frequency being selected from a multiplex of hologram frequencies by adjustment of a signal processing parameter.

11. The apparatus of claim 1, the apparatus being a coherent Stokes Raman scattering (CSRS) holography apparatus,
the FWM signal being a CSRS signal,
the third beam being an anti-Stokes beam.

12. A method of obtaining a four-wave mixing (FWM) image of a sample, the method comprising:
illuminating the sample with a first beam and a third beam so as to generate a FWM signal from the sample, wherein a frequency difference between said first beam and said third beam matches a resonant frequency of the sample;
providing a reference beam, the reference beam being frequency matched to the FWM signal;
combining the reference beam and the FWM signal so as to generate a FWM hologram of the sample;
detecting the FWM hologram using an imaging device; and
analyzing the detected FWM hologram to obtain an image of the sample.

13. The method of claim 12, the first beam and the second beam being provided by a single pump/probe beam comprising pulsed laser radiation,
the third beam being a Stokes beam or an anti-Stokes beam.

14. The method of claim 12, wherein the FWM hologram is a coherent anti-Stokes Raman hologram (CARS hologram),
the FWM signal being a CARS signal,
the third beam being a Stokes beam.

15. The method of claim 14, further including generating the Stokes beam and the reference beam using an optical parametric oscillator (OPO),
the OPO being tunable so as to adjust the frequencies of both the third beam and the reference beam simultaneously.

16. The method of claim 12, further comprising generating the reference beam using a nonlinear material located proximate the sample.

17. The method of claim 12, wherein the reference beam and at least one of the first beam, and the third beam are broadband beams, so as to simultaneously generate a plurality of FWM holograms having differing hologram carrier frequencies.

18. The method of claim 17, further comprising selecting a FWM hologram carrier frequency so as to form an image arising from a selected FWM process within the sample.

19. The method of claim 12, further including
detecting the FWM hologram using an electronic imaging device to obtain a hologram signal; and
creating an image of the sample by digital processing of the hologram signal.

20. The method of claim 19, the image corresponding to an image plane within the sample,
the method further comprising adjusting the location of the image plane by digital processing of the hologram signal.

21. The apparatus of claim 20, further comprising selecting a FWM hologram frequency from a plurality of hologram frequencies by signal processing of the hologram signal.

22. The method of claim 12, wherein the FWM hologram is a coherent Stokes Raman hologram (CSRS hologram), a stimulated Raman hologram, or a Brillouin scattering hologram.

23. The method of claim 12, the image being obtained using a single pulse of illumination.

24. The method of claim 12, further comprising obtaining a temporal sequence of FWM holograms to track a dynamic process within the sample.

* * * * *